(12) United States Patent
Jussila et al.

(10) Patent No.: US 6,258,586 B1
(45) Date of Patent: Jul. 10, 2001

(54) SOLID CULTURE MEDIUM FOR MICROORGANISMS, PROCESS FOR ITS PREPARATION, AND USE

(75) Inventors: Marita Jussila, Otalampi; Helena Tuompo; Leena Scheinin, both of Espoo, all of (FI)

(73) Assignee: Orion-Yhtyma Oyj, Espoo (FI)

( * ) Notice: Subject to any disclaimer, the term of this patent is extended or adjusted under 35 U.S.C. 154(b) by 0 days.

(21) Appl. No.: 09/093,623

(22) Filed: Jun. 1, 1998

Related U.S. Application Data

(63) Continuation of application No. PCT/FI98/00020, filed on Jan. 14, 1998.

(30) Foreign Application Priority Data

Jan. 15, 1997 (FI) ........................................... 970163

(51) Int. Cl.$^7$ ..................................... C12N 1/22
(52) U.S. Cl. ................... 435/252; 435/252.1; 524/916
(58) Field of Search .................... 435/252, 252.1, 435/397, 404; 524/916

(56) References Cited

U.S. PATENT DOCUMENTS

| | | |
|---|---|---|
| 3,046,201 | 6/1962 | White et al. . |
| 3,360,440 | 12/1967 | Haab et al. . |
| 3,814,670 | 6/1974 | Freake et al. . |
| 3,881,993 | 5/1975 | Freake et al. . |
| 5,089,413 | 2/1992 | Nelson et al. . |
| 5,336,614 | 8/1994 | Brown et al. . |
| 5,371,010 | 12/1994 | Brown et al. . |
| 5,494,823 | 2/1996 | Takemoto et al. . |
| 5,558,861 | 9/1996 | Yamanaka et al. . |

FOREIGN PATENT DOCUMENTS

| | | |
|---|---|---|
| 4206850A1 | 9/1993 | (DE) . |
| 0374901A1 | 6/1990 | (EP) . |
| 1295337 | 11/1972 | (GB) . |
| 2300648 | 11/1996 | (GB) . |
| WO8202563 | 8/1982 | (WO) . |
| WO9312218 | 6/1993 | (WO) . |

OTHER PUBLICATIONS

File, WPI, Derwent Accession No. 96–145944, abstract of JP08033486.
Anbergen et al. (1990) *Polymer* 31:1854.
Esposito et al. (1996) Chemical Abstracts 124:263718.
Esposito et al. (1996) Chemical Abstracts 125:36107.
Harsh et al. (1991) *Journal of Controlled Release* 17:175.

*Primary Examiner*—Leon B. Lankford, Jr.
(74) *Attorney, Agent, or Firm*—Baker Botts

(57) ABSTRACT

The object of the invention is a microbe culture medium which can be activated with a liquid sample or water. Covalently crosslinked cellulose ethers are used as a gelling agent. The gel into which nutrients have been mixed is dried on a water-impermeable support. The culture medium according to the invention may be utilized for detecting bacteria and fungi both in the hygiene control of industry and in medical diagnostics. The same method principle may be used within different sensitivity ranges as the absorption capacity of the gel may be regulated according to the hydrophilicity of cellulose ethers.

32 Claims, No Drawings

SOLID CULTURE MEDIUM FOR MICROORGANISMS, PROCESS FOR ITS PREPARATION, AND USE

This is a continuation of copending application Ser. No. PCT/FI98/0020 filed Jan. 14, 1998 which is incorporated by reference herein.

BACKGROUND OF THE INVENTION

The object of the invention is a ready-to-use culture medium for microorganisms, comprising nutrients and hydrogel based on cellulose ethers. The culture medium may be dried on a solid support, stored dry and moistened when taken into use, either directly with a sample to be tested or with water. Culture medium device may be immersed in a sample solution to be tested, or it may be pressed against a damp sample surface to be tested, after which the medium is incubated at a suitable temperature until microorganisms have grown to visually recognizable colonies.

The determination of the amount and species of the microorganisms which cause infections and contamination is important when either a suitable method of treatment in medication or a defensive method in food industry and elsewhere in the environmental hygiene is chosen. Several culture media and culture media devices for detecting various bacteria and fungi have been developed for this purpose.

In the microbiology that diagnoses diseases the aim is to determine and identify the microorganisms which cause infections, i.a. bacteria (both aerobic and anaerobic bacteria) and fungi (yeasts and molds), as exactly as possible from various samples of human and animal origin (e.g. urine, blood, serum, plasma, cerebral spinal fluid, pleural fluid, ascites fluid, pus, wound secretion, sputum, stool, and pharyngeal specimen) so as to be able to choose an effective, curative method of treatment. Often also the susceptibility of microbes to various antimicrobial drugs is to be determined. Various culture media and culture media devices are used for this purpose.

Microorganisms cause problems also in several different fields of industry. If they succeed in accumulating in processes, the health hazards and contamination problems caused by them will become difficult to handle. Usually microbes can effectively resist cleaning inside a so called biofilm layer composed of the solid material of microbe cells and process liquids, which layer gives protection against the effect of disinfectants and antiseptic agents, as well as against the effect of antibiotics, and inside which microbes may survive even for long periods of time.

Several production processes require a high hygienic level, because even a slight growth of microorganisms may ruin the whole product. Lowered hygiene causes problems especially in food industry, in health care, in medical treatment and in water systems. Other kinds of problems, such as slime formation caused by bacteria in the vessels and pipe systems of process industry, may occur especially in wood processing industry, and molds may appear everywhere in ventilation pipes. In industry it has been found that microbes contribute also to other problems, such as at the emergence of corrosion. Microbes and the problems caused by them are found also elsewhere, such as on the tiles of bathroom, on sauna benches and in swimming pools. In hospitals pathogenic microbes may e.g. colonize in a ventilation system and thus cause hospital infections. Therefore a continuous follow-up of hygiene by determining the amounts of microbes is in use in most facilities where the level of hygiene is to be realized.

The classical methods for culturing microorganisms are based on culture media where the gelling agent is agar-agar isolated from algae. Culture media have to be either prepared laboriously from a dry powder or bought in a ready-to-use form. Commercially available ready-to-use culture media are ready in swollen, wetted form. The storage time of self-made and of industrial, moist culture media which contain agar-agar is limited, because they dry easily and cannot be moistened again. In order to maintain moisture and sterility for as long as possible, this kind of culture media have to be stored in very tight packagings which need plenty of room.

In the culture medium of the U.S. Pat. No. 3,046,201, the gelling agents used instead of agar-agar include cross-linked polyacrylamide hydrogels or mixtures of polyacrylamide and gelatine, silica gel or starch. The gel is not dried and it does not have the property of absorbing sample liquid.

In the method according to the U.S. Pat. No. 3,360,440, a dry gel is prepared by mixing nutrients with cellulose ether and by lyophilizing the mixture. Before lyophilization, microorganisms may be added to the mixture, and thus a ready-to-use, preservable culture is obtained. The dry gel is resuspended with sterile water before it is used for the determination of microbes or, if microbes have been added before lyophilization, before growing of microbes. In microbe assays, the microbes of the sample are absorbed within the gel and grow thus differently as to their morphology compared to the growth on usual media where growth takes place on the surface of the gel. This considerably complicates the readability of the results and thus reduces the reliability of the assays. Further, lyophilization is a multistage process and requires relatively expensive equipment.

In the test kit according to said U.S. Pat. No. 3,360,440, water and the dried gel have been included in different parts of a reservoir. After resuspension the gel may be transferred on a desired support by pushing the reservoir wall. The test kit is complicated and is not ready-to-use.

GB 1 295 337 discloses a dehydrated hydrogel which is integrally bonded to a culturing container by means of radiation and which comprises e.g. crosslinked poly (ethylene oxide), polyvinyl pyrrolidone and polyvinyl alcohol. Nutrients are added to the gel immediately after its preparation or just prior to use.

In addition to this, methods are known where nutrients and gel are absorbed by an absorbing membrane, which may be a filter paper or other equivalent, absorbing support layer. The gel may also be spread on the surface of a membrane, or the gel is replaced by a membrane which is impermeable to bacteria. In these methods the absorbing membrane maintains inside itself the moisture needed for growth. Methods like this are disclosed in the patent publications U.S. Pat. No. 3,881,993, EP 0 374 905, U.S. Pat. No. 3,814,670 and EP 0 006 192, which are examined in more detail in the following.

In the method of the U.S. Pat. No. 3,881,993, nutrients, reagents and a gelling agent have been absorbed by an absorbing layer, which acts also as a supporting structure, and the medium has been dried under negative or positive pressure. As a gelling agent inert gum, linear polysaccharides or sodium alginate are used. In the method according to EP 0 374 905, gelling agents are absorbed by a filter paper. Sodium alginate is used as a gelling agent. The test medium according to the method is used wet. The method according to the U.S. Pat. No. 3,814,670 is similar to the above ones, with the exception that the gel layer is spread on the surface of an absorbing membrane. As a gelling agent agar, gelatine, cellulose gums, carrageens, alginates, albumins, polysaccharides or polypeptides may be used. The culture medium has been dried. EP 0 006 192 discloses a dry culture medium where a culture medium cartoon is covered by a plastic membrane, which is a homopolymer of vinylacetate or acrylic acid esters, a copolymer of vinylpropionate and vinylacetate, vinylpropionate and vinylchloride, vinylacetate and maleic acid esters, acrylnitrile, acrylic acid esters and vinylpropionate or butadiene and styrene. As an opening agent polyethyleneglycols, polyethyleneoxides, polyvinylpyrrolidone, polyvinylalcohols, partly saponified polyvinylesters, mixed polymers of vinylpyrrolidone and vinylesters, or cellulose derivatives, such as hydroxyalkyl cellulose, are used.

In the U.S. Pat. No. 5,494,823, a mixture comprising nutrients and a gelation agent is coated with an absorbent fibrous sheet into which the sample solution is dispersed by the phenomenon of capillary attraction. After the mixture containing the gelation agent has absorbed moisture and formed a gel, the fibers of the absorbent fibrous sheet are buried and adhered into the mixture.

JP 94-172178 discloses a cell culture carrier comprising two hydrogels, the other gel containing e.g. particles microbeads, fibre, sponge, etc. and functioning as a supporting structure.

A disadvantage with above mentioned methods is that the gelling agent of culture medium needs supporting layers to remain consistent, which makes even the preparation of media difficult. Those methods wherein the gelling agent is also absorbed by an absorbing layer further have the disadvantage that the surface on which microbes grow is rough, and thus to an observer the microbes look totally different from those growing on the surface of agar in a classical detection method.

Also known are culture media where gelling agents are powders which are soluble in cold water. They are attached on a hydrophobic support with the help of an adhesive layer, like in the U.S. Pat. No. 5,089,413 and U.S. Pat. No. 4,565,783, as well as in the Wo publication 93/12218. The culture medium often further comprises an air-permeable membrane. A hydrophobic support may be directly covered with the gel, whereby the gel has been crosslinked with ionic bonds by adding salts into the gel. Culture media like this have been used in the methods according to the U.S. Pat. No. 5,089,413 and 4,565,783 only as streakable media. However, a disadvantage is that when crosslinking is carried out with the help of salts, the growth of microbes is often inhibited.

In the methods according to the patents U.S. Pat. No. 5,089,413 and U.S. Pat. No. 4,565,783, copolymers of isooctylacrylate and acrylamide or acrylic acid, or copolymers of 2-methylbutylacrylate and acrylic acid or silicone gum are used as adhesives. As gelling powder, alginine, carboxymethyl cellulose, hydroxyethyl cellulose, guar gum, locust bean gum, xanthan gum or mixtures of these are used. In the method according to WO 93/12218, a copolymer of isooctylacrylate and acrylamide or N-vinylpyrrolidone is used as an adhesive layer. To this adhesive layer is attached a cold-water-soluble powder, which is a mixture of super absorbent and gelling agents. The gelling agent may be alginine, guar gum, hydroxymethyl cellulose, locust bean gum, carboxymethyl cellulose, xanthan gum or a mixture of these. The superabsorbent agent is a glycol modified polysaccharide, a graft polymer of starch and sodiumacrylate acrylamide or a mixture of these. Except of the streakable medium, in these methods microbes grow inside the gel. A disadvantage is therefore that the morphology of colonies is not similar to the morphology on agar-agar surfaces.

SUMMARY OF THE INVENTION

The purpose of the invention is to overcome the above mentioned problems and create a new culture medium device for culturing and identifying microorganisms.

The hydrogel culture medium which is the object of the invention is especially suitable to be used for the determination of microorganisms in samples of human and animal origin for verifying medical diagnosis and for choosing a method of treatment.

Another purpose of the invention is to achieve a solution for determining of microorganisms and biofilms formed by them, i.a. in the process vessels of food industry and wood processing industry and on the steel surfaces of ventilation systems.

The culture medium device which is the object of the invention is particularly suitable in situations where the preparation of culture media is not possible and where continuous follow-up of hygiene is needed, such as self-monitoring of food industry and the confirmation of the eradication of pathogenic bacteria in hospitals e.g. on various surfaces, in solutions and in ventilation systems.

The purpose has been to develop a culture medium device which renders it possible to achieve a better sensitivity towards different microbes but which can, however, by varying the ingredients of the culture medium and their proportions, be used within different sensitivity areas. In order to guarantee a long shelf-life the culture medium has to be in dry form. The culture medium has to be easy to use.

It has also been a purpose that nutrients and other reagents are added into the gel and that the gel can be attached directly on a water-impermeable support without absorbing support layers or adhesive layers.

A prerequisite is also that the gel functions like a filter, and thus microbes are adhered on the surface of the gel while the liquid from the sample is absorbed by the gel. Due to the liquid absorbed, nutrients dissolve and are diffused to be utilized by microbes, and thus microbes as to their morphology grow as on classical agar-agar media.

A purpose has been to develop an absorbing gel with a viscosity of 1 000–1 000 000 mPas (2% water solution, 20° C., 100 kPa), which after the addition of nutrients and other necessary components may be spread on a suitable support which is impermeable to water, dried under normal atmosphere to a moisture content of 0.01–20% by weight, as well as if necessary sterilized for example by radiation or gasification.

It has now been found that the above mentioned requirements can be fulfilled if crosslinked, cellulose ether based hydrogels are used as a gelling agent. They are hydrophilic polymers crosslinked with covalent bonds, and they swell in water but maintain their form due to their permanent three-dimensional structure, and thus do not need separate support layers or adhesive layers like the solutions according to the state of the art. Thus the hydrogel culture medium according to the invention may be dried on a water-repellant support without adhesive agents.

The amount of chemical crosslinks in cellulose ether gel may be used to regulate the filter properties of the gel. The more crosslinks there are in the gel, the smaller is its pore size. Microbes are attached on the surface of the gel while the liquid in the sample is absorbed by the gel, and thus the sample is concentrated. The absorbtion capacity of the gel and simultaneously the sensitivity of the culture medium may be regulated by choosing suitable mixtures of hydrophilic and hydrophobic cellulose ethers as starting materials (cellulose ethers containing e.g. a sodium acetate group or a hydroxyalkyl group are hydrophilic, and cellulose ethers containing e.g. an alkyl or benzyl group are hydrophobic). Due to the crosslinks and hydrophilicity/hydrophobicity properties of cellulose ethers, the gel may absorb a sample which is larger as regards its liquid volume and bacteria content.

DETAILED DESCRIPTION OF THE PREFERRED EMBODIMENTS

The culture medium having the basic composition according to the invention may be used within different sensitivity ranges. Thus it may be used to determine for example $1-10^3$ CFU/ml or $10^3$—over $10^7$ CFU/ml. The culture medium device according to the invention is thus very suitable to be used both in the hygiene control of industry and on the other hand in medical diagnostics.

When immersed into a sample, the dry culture medium according to the invention absorbs within a few minutes a constant amount of liquid (10–1000 $\mu$l depending on the sensitivity needed), which contains an equivalent amount of microbes compared to the sample to be tested. The culture medium moistened with a sample is as smooth and even as normal agar-agar media, and after normal incubation time microbes form colonies on the surface of the gel.

The rigidity of the gel surface to be formed and the viscosity properties of the gel may be regulated by using as starting materials cellulose ethers with different molecular weights and viscosities.

Among the advantages of cellulose ethers are also that the gels prepared from them are bright and transparent, the raw materials are cheap bulk products and as natural polymers do not harm the environment when decomposed.

Cellulose derivatives where hydrogen atoms in the OH groups of cellulose have been replaced by alkyl, such as methyl, ethyl, or propyl groups, hydroxyalkyl, such as hydroxyethyl or hydroxypropyl groups, benzyl or hydroxybenzyl groups or alkalimetal salts of carboxymethyl, such as sodium acetate, or mixtures of these, may be used as cellulose ethers. Each glucose unit of cellulose may contain 0–3 OH groups substituted with above mentioned groups. The viscosity of cellulose ethers may be 100–100 000 mPas, preferably 1 000–10 000 mPas (2% water solution, temperature 20° C., pressure 100 kPa) and molecular weight 500–1 000 000, preferably 1 000–500 000. When cellulose ethers having above mentioned viscosities are used as starting materials, the viscosity of the end product is within the desired viscosity range of 1 000–1 000 000 mpas.

Cellulose ethers are linear polymers which may be used to form hydrogels by crosslinking them in different ways. Cellulose ethers may be crosslinked by methods known for cellulose. Thus a three-dimensional net polymer may be obtained for example a) by letting the OH groups of cellulose ethers react with formaldehyde, glyoxal, urea, or monomethylol and dimethylol derivatives of melamine, ureaformaldehyde and melamine formaldehyde prepolymers, dimethylolethyleneurea, epichlorohydrin, diepoxides, diisocyanates (George Odian Principles of Polymerization 1981, 671, John Wiley & Sons, Inc.) or divinylsulphone (David C. Harsh and Stevin H. Gehrke; Journal of Controlled Release, 17 (1991) 175–186 and U. Anbergen and W. Oppermann; Polymer, Vol 31, 1990, 1854–1858), b) by radiation (i.a. electrons, neutrons, gamma and UV radiation) (George Odian Principles of Polymerization 1981, 671–672, John Wiley & Sons, Inc.) or c) by graftpolymerizing cellulose ethers with vinyl monomers according to the free radical mechanism. Free radicals are produced either by radiation (e.g. gamma or UV radiation) or by chemical activation (redox system, peroxides or diazonium salts) (A. Hebeish, J. T. Guthrie, The Chemistry and Technology of Cellulosic Copolymers, 1981, 32–241, Springer-Verlag). For example acroleine, acrylamide, 2-acrylamido-2-methylpropane sulfonic acid, salts of 2-acrylamido-2-methylpropane sulfonic acid, acrylic acid, salts of acrylic acid, acrylonitrile, methacrylamide, methacrylamidopropyl trimethyl ammonium chloride, methacrylic acid, salts of methacrylic acid, 2-metacroyloxyethane sulfonic acid, salts of 2-metacroyloxyethane sulfonic acid, 2-methacryloxyethyl trimethyl ammonium chloride, 3-methacryloxy-2-hydroxypropyl trimethyl ammonium chloride, methacroloylchloride, N,N'-methylene bisacrylamide, or mixtures of these may be used.

Cellulose ethers can thus be crosslinked for example with divinylsulphone in an alkaline solution. Divinylsulphone forms crosslinks by an addition reaction with OH groups situated either in the polymer backbone or in the substituted groups. The amount of divinylsulphone used may be chosen according to the desired crosslink density and the reactivity and concentration of the polymers to be cross-linked and is for methyl cellulose, hydroxypropyl cellulose and carboxymethyl cellulose about 0.005–1.5 g divinylsulphone per one gram of dry polymer, preferably about 0.05–0.5 g divinylsulphone per one gram of dry polymer, in a 2% cellulose ether solution. The theoretical crosslink density, when cross-linking is carried out with divinylsulphone or some other compound mentioned above under alternative a), is about $8.5 \times 10^{-5}$–$2.5 \times 10^{-2}$ moles per one gram of dry cellulose ether, preferably about $8.5 \times 10^{-4}$–$8.5 \times 10^{-3}$ moles per one gram of dry cellulose ether.

In the culture medium according to the invention the pore size of the hydrogel based on crosslinked cellulose ethers is about 0.1–1000 nm, preferably about 1.0–500 nm.

The absorption properties of hydrogels may be improved by adding detergents. As detergents anionic (for example sodiumlaurylsulphate) or nonionic (e.g. Tween 20, Triton X-100) detergents may be used. Absorption properties of hydrogels may also be regulated with other gelling, water solutions absorbing compounds, such as the above mentioned cellulose ethers, copolymers of above mentioned polymers used in graftpolymerization, agar-agar, albumins, alginates, gelatine, guar gum, carrageens, xanthan gum, polypeptides and other modified polysaccharides.

In addition to possible detergents and gelling agents, nutrients (i.a. peptones, nutrient hydrolysates and sugars) and, if desired, pH regulators, substrates, other reagents relating to biochemical detection reactions, selective inhibitors, antibiotics and coloring agents are added to the gel before the gel mixture is dried.

The cellulose ether based hydrogel culture medium thus obtained may be spread on a suitable water-impermeable support and dried to a moisture content of 0.01–20% by weight. Suitable water-impermeable supports are for example those of polypropene, polystyrene or polyester, of which test strips of the dip-slide-type may be prepared. If desired, the culture medium may also be dried on a glass fibre mesh, if the mesh is suitably fine and cross-linking of the hydrogel is sufficient. Drying may be performed under normal atmosphere or, if desired, under negative or positive pressure. Suitable final moisture content is 0.01–20% by weight, preferably 0.05–10% by weight.

The dry culture medium remains usable for long periods of time, and its applications are diversified. Thus a dry culture medium device may be immersed directly into a sample solution to be tested or pressed against a damp sample surface to be tested, whereby the gel absorbs a constant amount of sample. If the object to be examined is a dry surface, the gel may first be wetted for example with water, and then pressed against the surface to be tested, or the surface may be moistened and then a dry gel pressed against said moistened surface. A dry solid sample on the other hand may be suspended into liquid, into which the culture medium device is dipped. A dry culture medium may also be moistened, and then the sample to be examined may be dropped on the medium.

A further object of the invention is a microbiological test kit comprising a dry hydrogel culture medium device wherein the gelling agent of the culture medium comprises a hydrogel according to the invention, based on covalently crosslinked cellulose ethers. The test kit may further comprise for example a wetting liquid and a sampling liquid. The packaging of the test strip may also be used as an incubation chamber.

Based on the above, the culture medium composition according to the invention may, when divinylsulphone is used for crosslinking, contain for example (percentages w/v calculated on the liquid volume)
 a) 0.1–10% by weight of sodium carboxy methyl cellulose
 b) 0.1–10% by weight of hydroxy propyl methyl cellulose or hydroxy propyl cellulose
 c) 0.05–0.5% by weight of sodium hydroxide
 d) 0.005–1.5 g divinylsulphone/g cellulose ether
 e) 0.01–1.0% by weight of Tween 20
 f) 0.1–10% by weight of yeast extract
 g) 0.1–10% by weight of Lablemco and
 h) 0.001–0.005% by weight of Bromthymol blue,
which mixture is spread on a water-impermeable support and dried at 20–60° C. to a moisture content of 0.01–20% by weight.

If cellulose ethers are crosslinked by graftpolymerization, the culture medium composition according to the invention may comprise for example (percentages w/v calculated on the liquid volume)
 a) 0.1–10% by weight of sodium carboxy methyl cellulose
 b) 0.1–10% by weight of acrylamide
 c) 0.01–10% by weight of N,N'-bismethylene acrylamide
 d) 0.001–0.1% by weight potassium hydroxide
 e) 0.001–0.01% by weight of sodiumpyrosulphite
 f) 0.005–0.1% by weight of potassium persulphate and
 g) 0.1–10% by weight of BHI nutrient,
which is spread on a water-impermeable support and dried at 20–60° C. to a moisture content of 0.01–20% by weight. In the above disclosed composition potassium persulphate and sodium pyrosulphite function as redox initiators of graftpolymerization under alkaline conditions, where acrylamide and N,N'-bismethylene acrylamide polymerize with cellulose ethers.

In the following the invention is further described with the help of working examples. The applications are examples and their purpose is in no way to limit the invention.

Microbes have been cultured using prior art technique in BHI solution, and cultures have been diluted to suspension series (CFU/ml). The microbes in suspension have been determined on the novel solid medium and compared to the prior art culture techniques, such as nutrient agar plate culture and dip slide (Uricult™, Hygicult™)

EXAMPLE 1

450 mg sodium hydroxide is dissolved into 400 ml of ion-exchanged water. To this is dissolved 2 g hydroxy propyl methyl cellulose (viscosity 4000 mPas, 2% solution) or hydroxy propyl cellulose (molecular weight 370 000) and 4 g of sodium carboxy methyl cellulose (viscosity 6000 mPas, 1% solution). The mixture is stirred for 3 hours at 60° C., cooled to room temperature and 0.4 ml of divinylsulphone is added, mixed and left standing for 16 hours. After stirring for 2 hours at 60° C., the gel is diluted to 1% and pH is adjusted with sodium hydroxide to pH 7. 0.05 g Tween 20, 0.6 g yeast extract, 0.3 g Lablemco and 3 mg Bromthymol blue are added into 100 ml of the above mentioned gel. The mixture obtained is dried on a polypropene support (200 $\mu$l/cm$^2$) at room temperature, and the dry culture medium thus obtained is cut into test strips of 12 cm$^2$.

EXAMPLE 2

12 g of sodium carboxy methyl cellulose (viscosity 6000 mPas 1% solution) is dissolved into 600 ml of water and gasified with inert gas and heated to 70° C. To the mixture is added 0.6 g N,N'-bismethylene acrylamide and 0.6 g acrylamide which have been dissolved into 20 ml of water. 1 ml 1 M potassium hydroxide solution, 35 mg sodium pyrosulphite are added and polymerized by adding 100 mg potassium persulphate. Stirring is continued under inert gas atmosphere for 4 hours. 15 g BHI nutrient is added to the mixture, pH is adjusted to pH 7 and the mixture is dried on a polypropene support (200 $\mu$l/cm$^2$) at room temperature, and the dry culture medium support thus obtained is cut into test strips of 12 cm$^2$.

EXAMPLE 3

The absorption capacity of test strips was tested by dipping the test strips from examples 1 and 2 into 0.9% NaCl solution for 0.5, 1.0, 1.5, 2.0 and 2.5 minutes and by weighing the strips. The results are presented in Table 1.

TABLE 1

Liquid absorption capacity of test strips

| Gel | Absorption time min/amount of absorbed liquid ml | | | | |
|---|---|---|---|---|---|
| | 0.5 min | 1.0 min | 1.5 min | 2.0 min | 2.5 min |
| 1 | 0.26 ml | 0.39 ml | 0.41 ml | 0.46 ml | 0.49 ml |
| 2 | 0.23 ml | 0.34 ml | 0.40 ml | 0.45 ml | 0.49 ml |
| 3 | 0.38 ml | 0.54 ml | 0.62 ml | 0.69 ml | 0.75 ml |

Gel 1 = Sodium carboxy methyl cellulose-hydroxy propyl methyl cellulose hydrogel (Ex. 1)
Gel 2 = Sodium carboxy methyl cellulose-hydroxy propyl cellulose hydrogel (Ex. 1)
Gel 3 = Graft sodium hydroxy propyl methyl cellulose acrylamide-N,N'-bismethylene acrylamide polymer (Ex. 2)

As a conclusion from the results it can be established that the gels synthesized of more hydrophilic cellulose ethers absorb more liquid within the same time.

EXAMPLE 4

The sodium carboxy methyl cellulose—hydroxy propyl methyl cellulose test strips from Example 1 were immersed for half a minute into a *Escherichia coli* (ATCC 25922) dilution series $10^1$–$10^8$ CFU/ml. 0.25 ml of the sample was absorbed. The test strips were incubated at 37° C. for 20 hours. Comparison was made to a nutrient agar plate inoculated with 0.1 ml of sample. Growth densities were calculated as from nutrient agar plates. The results were collected in Table 2.

TABLE 2

Growth densities of *Escherichia coli* on nutrient agar plates and test strips

| bacterial dilution | Growth density CFU/ml on nutrient agar plate | Growth density CFU/ml on test strip |
|---|---|---|
| $10^1$ | 3 | 8 |
| $10^2$ | 18 | 38 |
| $10^3$ | $10^3$ | $10^4$ |
| $10^4$ | $10^4$ | $10^5$ |
| $10^5$ | $10^5$ | $10^7$ |
| $10^6$ | $10^6$ | >$10^7$ |
| $10^7$ | >$10^7$ | >$10^7$ |
| $10^8$ | >$10^7$ | >$10^7$ |

From the growth densities of Table 2 it can be found that growth density is in proportion to the amount of sample.

EXAMPLE 5

The performance of the sodium carboxy methyl cellulose—hydroxy propyl methyl cellulose test strips of Example 1 was studied with different bacteria and yeast. The test strips were immersed for half a minute in the dilution series of *Escherichia coli* (ATCC 25922), *Klebsiella pneumoniae* (ATCC 33495), *Proteus mirabilis* (ATCC 12453), *Pseudomonas aeruginosa* (ATCC 27853), *Enterococcus faecalis* (ATCC 29212), *Staphylococcus aureus* (ATCC 25922) and *Candida albicans* (ATCC 14053) in $10^1$–$10^8$ CFU/ml. 0.25 ml of the sample was absorbed. The test strips were incubated at 37° C. for 20 hours. The Cled-medium of the Uricult™ dip slide was used as a comparison with a sample amount of 0.025 ml. Growth densities were read by comparing to a Uricult model chart. The results were collected in Table 3.

TABLE 3

Growth densities of various microbes on test strips and on the Cled-medium of Uricult™

| Microbe/Test strip/Uricult™-Cled | $10^1$ | $10^2$ | $10^3$ | $10^4$ | $10^5$ | $10^6$ | $10^7$ | $10^8$ |
|---|---|---|---|---|---|---|---|---|
| *E. coli* | | | | | | | | |
| Test strip | 8 | 38 | $10^4$ | $10^5$ | $10^7$ | >$10^7$ | >$10^7$ | >$10^7$ |
| Uricult™-Cled | 0 | 1 | 6 | $10^4$ | $10^{4-5}$ | $10^6$ | $10^7$ | >$10^7$ |
| *K. pneumoniae* | | | | | | | | |
| Test strip | 4 | $10^{3-4}$ | $10^4$ | $10^{5-6}$ | >$10^7$ | >$10^7$ | >$10^7$ | >$10^7$ |
| Uricult™-Cled | 1 | 2 | $10^3$ | $10^4$ | $10^5$ | $10^6$ | $10^7$ | >$10^7$ |
| *P. mirabilis* | | | | | | | | |
| Test strip | 14 | 39 | $10^4$ | $10^5$ | >$10^7$ | >$10^7$ | >$10^7$ | >$10^7$ |
| Uricult™-Cled | 5 | 5 | 7 | $10^{3-4}$ | $10^4$ | $10^5$ | $10^6$ | $10^7$ |
| *P. aeruginosa* | | | | | | | | |
| Test strip | 6 | 17 | $10^4$ | $10^{5-6}$ | >$10^7$ | >$10^7$ | >$10^7$ | >$10^7$ |
| Uricult™-Cled | 0 | 2 | 10 | $10^4$ | >$10^7$ | >$10^7$ | >$10^7$ | >$10^7$ |
| *S. aureus* | | | | | | | | |
| Test strip | 1 | 2 | 18 | $10^4$ | $10^5$ | $10^{5-6}$ | >$10^7$ | >$10^7$ |
| Uricult™-Cled | 0 | 0 | 10 | $10^{3-4}$ | $10^{4-5}$ | $10^{5-6}$ | $10^6$ | $10^7$ |
| *E. faecalis* | | | | | | | | |
| Test strip | 1 | $10^{3-4}$ | $10^4$ | $10^{4-5}$ | >$10^7$ | >$10^7$ | >$10^7$ | >$10^7$ |
| Uricult™-Cled | 0 | 1 | 3 | $10^{3-4}$ | $10^4$ | $10^{5-6}$ | $10^6$ | >$10^7$ |
| *C. albicans* | | | | | | | | |
| Test strip | 0 | 0 | 0 | 20 | $10^{5-6}$ | >$10^7$ | >$10^7$ | >$10^7$ |
| Uricult™-Cled | 0 | 0 | 1 | $10^3$ | $10^4$ | $10^5$ | $10^{5-6}$ | $10^6$ |

Microbial growth was even hundred times more dense on the test strips because more sample was absorbed by them than by the Cled-medium.

EXAMPLE 6

The performance of the sodium carboxy methyl cellulose—hydroxy propyl methyl cellulose test strips of Example 1 was examined with yeast and mold. The test strips were immersed for two minutes in dilution series of *Candida albicans* (ATCC 14053) and *Aspergillus niger* in $10^1$–$10^6$ CFU/ml. 0.45 ml of the sample was absorbed. The test strips were incubated at 37° C. for 20 hours (*C. albicans*) or at 22° C. for 72 hours (*A. niger*). Hygicult™ Y & F was used as a comparison with a sample amount of 0.050 ml. Growth densities were read by comparing to a model chart of Hygicult.

TABLE 4

Growth densities of yeast and mold on test strips and on Hygicult™ Y & F.

| Microbe | $10^1$ | $10^2$ | $10^3$ | $10^4$ | $10^5$ | $10^6$ |
|---|---|---|---|---|---|---|
| *C. albicans* | | | | | | |
| Test strip Hygicult™ Y & F | 0 | 2 | 50 | 300 | $10^{4-5}$ | >$10^7$ |
| Hygicult™ Y & F | 0 | 3 | 1 | 32 | $10^4$ | $10^6$ |

TABLE 4-continued

Growth densities of yeast and mold on test strips and on Hygicult™ Y & F.

*A. niger*

| | | | | | | |
|---|---|---|---|---|---|---|
| Test strip | 0 | 1 | 0 | 2 | 6 | 18 |
| Hygicult™ Y & F | 0 | 0 | 1 | 6 | 36 | $10^{4-5}$ |

Hydrogel culture medium based on crosslinked cellulose ethers maintains the growth of molds and yeast, although in this example the nutrients of the culture medium are not optimal to yeast nor mold as in Hygicul™ Y & F.

EXAMPLE 7

The performance of different hydrogel culture media based on cellulose ethers was examined by immersing the culture medium strips for half a minute in a dilution series of *Escherichia coli* (ATCC 25922), *Enterococcus faecalis* (ATCC 29212) and *Candida albicans* (ATCC 14053) in $10^1$–$10^4$ CFU/ml and by incubating at 37° C. for 20 hours. Growth densities were read by comparing to the model chart of Uricult™. The results were collected in Table 5.

TABLE 5

Growth densities of *Escherichia coli, Enterococcus faecalis* and *Candida albicans*, CFU/ml, on various hydrogel culture media

| | Microbial dilution CFU/ml | | | | | | | | | | | |
|---|---|---|---|---|---|---|---|---|---|---|---|---|
| | *E. coli* | | | | *E. faecalis* | | | | *C. albicans* | | | |
| Gel | $10^1$ | $10^2$ | $10^3$ | $10^4$ | $10^1$ | $10^2$ | $10^3$ | $10^4$ | $10^1$ | $10^2$ | $10^3$ | $10^4$ |
| 1 | 8 | 38 | $10^4$ | $10^5$ | 1 | $10^3$ | $10^4$ | $10^5$ | 0 | 0 | 0 | 20 |
| 2 | 16 | 49 | $10^4$ | $10^5$ | 2 | 21 | $10^4$ | $10^5$ | 0 | 2 | 20 | $10^4$ |
| 3 | 1 | 54 | $10^4$ | $10^5$ | 7 | 35 | $10^4$ | $10^5$ | 0 | 4 | 30 | $10^4$ |

Gel 1=Sodium carboxy methyl cellulose—hydroxy propyl methyl cellulose hydrogel (Ex. 1)

Gel 2=Sodium carboxy methyl cellulose—hydroxy propyl cellulose hydrogel (Ex. 1)

Gel 3=Graft sodium hydroxy propyl methyl cellulose acrylamide—N,N'-bismethylene acrylamide polymer (Ex. 2).

From the examples of Table 5 it is seen that hydrogels prepared from different cellulose ethers maintain microbial growth.

As a summary from above examples it may be stated that—all microbes grow on the culture medium according to the invention, although the culture medium composition of the examples was not at all optimized for different microbes, the culture medium according to the invention is generally more sensitive than nutrient agar or commercially available dip slides, growth on the culture medium according to the invention is proportional to the amount of sample.

What is claimed is:

1. Dried hydrogel culture medium for microbes comprising a hydrogel including covalently crosslinked cellulose ethers wherein the viscosity of the hydrogel at 20° C. is in the range of 1000 to 1,000,000 mPas.

2. Dried hydrogel culture medium according to claim 1 wherein the cellulose ethers include both hydrophobic and hydrophilic cellulose ethers.

3. Dried hydrogel culture medium according to claim 1 or claim 2 wherein the cellulose ethers include glucose units having OH groups and up to three OH groups in each glucose unit are substituted with at least one selected from the group consisting of alkyl, hydroxyalkyl, benzyl, hydroxybenzyl and alkalimetal salt of carboxymethyl.

4. Dried hydrogel culture medium according to claim 3 wherein the alkyl group is selected from the group consisting of methyl, ethyl and propyl.

5. Dried hydrogel culture medium according to claim 3 wherein the hydroxyalkyl group is selected from the group consisting of hydroxyethyl and hydroxypropyl.

6. Dried hydrogel culture medium according to claim 1 or claim 2 wherein the molecular weight of the cellulose eithers is in the range of 500 to 1,000,000.

7. Dried hydrogel culture medium according to claim 6 wherein the molecular weight of the cellulose ethers is in the range of 1,000 to 500,000.

8. Dried hydrogel culture medium according to claim 3 wherein the molecular weight of the cellulose ethers is in the range of 500 to 1,000,000.

9. Dried hydrogel culture medium according to claim 8 wherein the molecular weight of the cellulose ethers is in the range of 1,000 to 500,000.

10. Dried hydrogel culture medium according to claim 4 wherein the molecular weight of the cellulose ethers is in the range of 500 to 1,000,000.

11. Dried hydrogel culture medium according to claim 10 wherein the molecular weight of the cellulose ethers is in the range of 1,000 to 500,000.

12. Dried hydrogel culture medium according to claim 5 wherein the molecular weight of the cellulose ethers is in the range of 500 to 1,000,000.

13. Dried hydrogel culture medium according to claim 12 wherein the molecular weight of the cellulose ethers is in the range of 1,000 to 500,000.

14. Dried hydrogel culture medium according to claim 1 or claim 2 wherein the viscosity of a 2% solution of the cellulose ethers at 20° C. is in the range of 100 to 100,000 mPas.

15. Dried hydrogel culture medium according to claim 14 wherein the viscosity of a 2% solution of the cellulose ethers at 20° C. is in the range of 1,000 to 10,000 mPas.

16. Dried hydrogel culture medium according to claim 4 wherein the viscosity of a 2% solution of the cellulose ethers at 20° C. is in the range of 100 to 100,000 mPas.

17. Dried hydrogel culture medium according to claim 16 wherein the viscosity of a 2% solution of the cellulose ethers at 20° C. is in the range of 1,000 to 10,000 mPas.

18. Dried hydrogel culture medium according to claim 5 wherein the viscosity of a 2% solution of the cellulose ethers at 20° C. is in the range of 100 to 100,000 mPas.

19. Dried hydrogel culture medium according to claim 18 wherein the viscosity of a 2% solution of the cellulose ethers at 20° C. is in the range of 1,000 to 10,000 mPas.

20. Dried hydrogel culture medium according to claim 1 or claim 2 wherein the pore size of the hydrogel is in the range of 0.1 to 1,000 mm.

21. Dried hydrogel culture medium according to claim 20 wherein the pore size of the hydrogel is in the range of 1.0 to 500 mm.

22. Dried hydrogel culture medium according to claim 4 wherein the pore size of the hydrogel is in the range of 0.1 to 1,000 mm.

23. Dried hydrogel culture medium according to claim 5 wherein the pore size of the hydrogel is in the range of 1.0 to 500 mm.

24. Dried hydrogel culture medium according to claim 5 wherein the pore size of the hydrogel is in the range of 0.1 to 1,000 mm.

25. Dried hydrogel culture medium according to claim 24 wherein the pore size of the hydrogel is in the range of 1.0 to 500 mm.

26. Dried hydrogel culture medium according to claim 1 or claim 2 further comprising nutrients and optionally at least one selected from the group consisting of other gelling agents, pH regulators, detergents, substrates, reagents used in detecting biochemical reactions, selective inhibitors and coloring agents.

27. Dried hydrogel culture medium according to claim 4 further comprising nutrients and optionally at least one selected from the group consisting of other gelling agents, pH regulators, detergents, substrates, reagents used in detecting biochemical reactions, selective inhibitors and coloring agents.

28. Dried hydrogel culture medium according to claim 5 further comprising nutrients and optionally at least one selected from the group consisting of other gelling agents, pH regulators, detergents, substrates, reagents used in detecting biochemical reactions, selective inhibitors and coloring agents.

29. Dried hydrogel culture medium according to claim 1 or claim 2 further comprising a water-impermeable support and wherein the hydrogel has been dried on the water-impermeable support to a moisture content in the range of 0.01 to 20% by weight.

30. Dried hydrogel culture medium according to claim 4 further comprising a water-impermeable support and wherein the hydrogel has been dried on the water-impermeable support to a moisture content in the range of 0.01 to 20% by weight.

31. Dried hydrogel culture medium according to claim 5 further comprising a water-impermeable support and wherein the hydrogel has been dried on the water-impermeable support to a moisture content in the range of 0.01 to 20% by weight.

32. Dried hydrogel culture medium according to claim 1 further comprising at least one selected from the group consisting of cellulose ethers, agar-agar, albumins, alginates, gelatine, guar gum, carrageens, xanthan gum, polypeptides, copolymers polymerized from vinyl monomers such as acroleine, acrylainide, 2-acrylamido-2-methylpropane sulfonic acid, salts of 2-acrylamido-2-methylpropane sulfonic acid, acrylic acid, salts of acrylic acid, acrylonitrile, methacrylamide, methacrylamidopropyl trimethyl ammonium chloride, methacrylic acid, salts of methacrylic acid, 2-metacroyloxyethane sulfonic acid, salts of 2-metacroyloxyetlhane sulfonic acid, 2-methacryloxyethyl trimethyl ammonium chloride, 3-metlhacryloxy-2-hydroxypropyl trimethyl ammonium chloride, methacroylchloride, N,N$^1$-methylene bisacrylamide or mixtures of these, or other modified polysaccharides.

* * * * *